US00PP17833P2

(12) United States Plant Patent
Irie

(10) Patent No.: US PP17,833 P2
(45) Date of Patent: Jun. 26, 2007

(54) ***HYDRANGEA* PLANT NAMED 'RIE 12'**

(50) Latin Name: *Hydrangea macrophylla*
Varietal Denomination: RIE 12

(76) Inventor: Ryoji Irie, 3-7 Narutaki Honmachi Ukyoku, Kyoto (JP)

( * ) Notice: Subject to any disclaimer, the term of this patent is extended or adjusted under 35 U.S.C. 154(b) by 0 days.

(21) Appl. No.: 11/334,074

(22) Filed: Jan. 19, 2006

(51) Int. Cl.
*A01H 5/00* (2006.01)

(52) U.S. Cl. ..... Plt./250

(58) Field of Classification Search ..... Plt./250
See application file for complete search history.

*Primary Examiner*—Kent Bell
*Assistant Examiner*—Annette H Para

(57) ABSTRACT

A new cultivar of *Hydrangea* plant named 'RIE 12' that is characterized by broad upright habit, large dark grey-green leaves, flowers that range in color from yellow-green to light and dark pink, and unique inflorescence development. In combination these traits set 'RIE 12' apart from all other existing varieties of *Hydrangea* known to the inventor.

2 Drawing Sheets

Genus: *Hydrangea.* Species: *macrophylla.*
Denomination: 'RIE 12'.

BACKGROUND OF THE INVENTION

The present invention relates to a new and distinct cultivar of *hydrangea* that is grown for use as an indoor floral potted plant and an outdoor ornamental flowering shrub. The new cultivar is known botanically as *Hydrangea macrophylla* and will be referred to hereinafter by the cultivar name 'RIE 12'.

'RIE 12' resulted from a breeding program that was conducted by the inventor at the inventor's nursery in Kyoto, Japan and began in 1990. The purpose of the breeding program was to produce new varieties of floral potted *hydrangeas* that exhibit new and unique flowers and flower color.

Between May 1990 and May 1993 the inventor assembled a collection of unnamed and unreleased hybrids from a sequence of deliberate pollinations involving the following cultivars, all unpatented, and available in commerce in Japan: *Hydrangea macrophylla* 'Otafuku', *Hydrangea macrophylla,* 'Yamaajisai', and *Hydrangea macrophylla* 'Fijinishiritaki'. The inventor did not record which variety was used as male parent and which as female parent. In May 1993, the inventor carried out a deliberate pollination between one unnamed plant from the inventor's collection as female parent and the variety *Hydrangea macrophylla* 'Sumidanohanabi' (unpatented) as male parent.

The pollination described above produced thirty-five individual varieties, which the inventor considered novel and unusual. One of these individual varieties was selected by the inventor in June 1994 and is the subject of the present invention, 'RIE 12'.

'RIE 12' is a deciduous shrub that exhibits large dark grey-green leaves and individual flowers that range in color from yellow-green to light and dark pink. Selection was based on the distinguishing characteristics of flowers, flower color, and inflorescence development. 'Lace cap' type *hydrangeas* produce showy sterile flowers along the outside of the inflorescence, and small inner flowers that are fertile flowers. When an individual inflorescence of 'RIE 12' first opens, it looks like a 'lace cap' type inflorescence with large sterile flowers on the edge. However, unlike the 'lace cap' type *Hydrangea,* the inflorescence eventually fills out completely. Within the inflorescence, center fertile flowers are intermixed with center sterile flowers, so that as the inflorescence develops further, the sterile flowers in the center open fully to then cover the smaller fertile flowers. 'RIE 12' is distinguishable from the parent plants by flower color, and unique inflorescence development, which produces an average of 190 sterile flowers and 175 fertile flowers per inflorescence.

The inventor considers that 'RIE 12' is distinct from other varieties of *Hydrangea* known to the inventor in the following respects:

First, whereas other varieties of *Hydrangea* in commerce have four petals per floret on a flat, one-dimensional plane, 'RIE 12' has two to three layers of petals per floret, creating a double-flower appearance.

Second, whereas many novel varieties have been found in, or brought from, Japan in recent years, none appear to have the combination of uniqueness of flower form as above combined with greater vigor and faster growing to flowering stage which typifies 'RIE 12'.

Third, the vigor of 'RIE 12' is evident in its strong thick stems which do not require staking to support the heavy blooms. 'RIE 12', although vigorous, exhibits a shorter internode distance than many other commercial forms of *Hydrangea,* allowing 'RIE 12' to be grown commercially with less or even no application of growth regulating chemical.

'RIE 12' was first asexually propagated by the inventor, in the spring of 1995 in a cultivated area of Kyoto, Japan. The method used for asexual propagation was softwood cuttings. The characteristics of the new *Hydrangea* cultivar named 'RIE 12' have been determined stable and are reproduced true to type in successive generations of asexual propagation.

SUMMARY OF THE INVENTION

The following traits have been repeatedly observed and represent the characteristics of the new *Hydrangea* cultivar 'RIE 12'. These traits in combination distinguish 'RIE 12' from all other commercial varieties of *Hydrangea* known to the inventor. 'RIE 12' has not been tested under all possible conditions and phenotypic differences may be observed with variations in environmental, climatic and cultural conditions, without however, any difference in genotype.

1. *Hydrangea* 'RIE 12' is grown for use as both an indoor floral potted plant and an outdoor ornamental flowering shrub.
2. *Hydrangea* 'RIE 12' exhibits individual flowers that range in color from yellow-green to light and dark pink.
3. *Hydrangea* 'RIE 12' exhibits unique inflorescence development that produces an average of 190 sterile flowers and 175 smaller fertile flowers per inflorescence.
4. *Hydrangea* 'RIE 12' exhibits a broad upright habit.
5. *Hydrangea* 'RIE 12' exhibits large dark grey-green leaves.
6. *Hydrangea* 'RIE 12' is 45 cm. in height and 61.6 cm. in diameter in a 5-liter container.
7. *Hydrangea* 'RIE 12' is a shrub.
8. *Hydrangea* 'RIE 12' is deciduous.
9. *Hydrangea* 'RIE 12' performs best when planted in loam based moisture retentive soil, in partial shade, with regular water.
10. *Hydrangea* 'RIE 12' is asexually propagated by the method of softwood cuttings.
11. *Hydrangea* 'RIE 12' exhibits rigid, strong basal branches.
12. *Hydrangea* 'RIE 12' is hardy to USDA Zone 7.
13. *Hydrangea* 'RIE 12' blooms continuously from early April to October.

BRIEF DESCRIPTION OF THE DRAWINGS

The accompanying color drawings illustrate the overall appearance of the new *Hydrangea* cultivar 'RIE 12' showing the colors as true as it is reasonably possible to obtain in colored reproductions of this type. Colors in the photographs may differ from the color values cited in the detailed botanical description, which accurately describe the actual colors of the new variety of *Hydrangea* named 'RIE 12'.

The drawing labeled as FIG. 1 depicts an individual whole plant growing in a 3-liter container in a frost-protected greenhouse in De Kwakel, The Netherlands. Plants were grown in peat moss soil with a pH of 6.0 to 6.4. The plant is approximately two years old. The plant was produced from a cutting which was rooted and grown in a four inch container, then transplanted into the 3 liter container, then pinched to encourage basal branching, then allowed to shoot from the base and allowed to flower in its natural season. The plant was pruned back to the base after flowering. The drawing depicts the vigorous basal branching habit of 'RIE 12' in its second season of re-growth. Such a plant would be highly suitable for use as a stock plant for the purpose of providing cutting material for commercial propagation.

Figure 1:
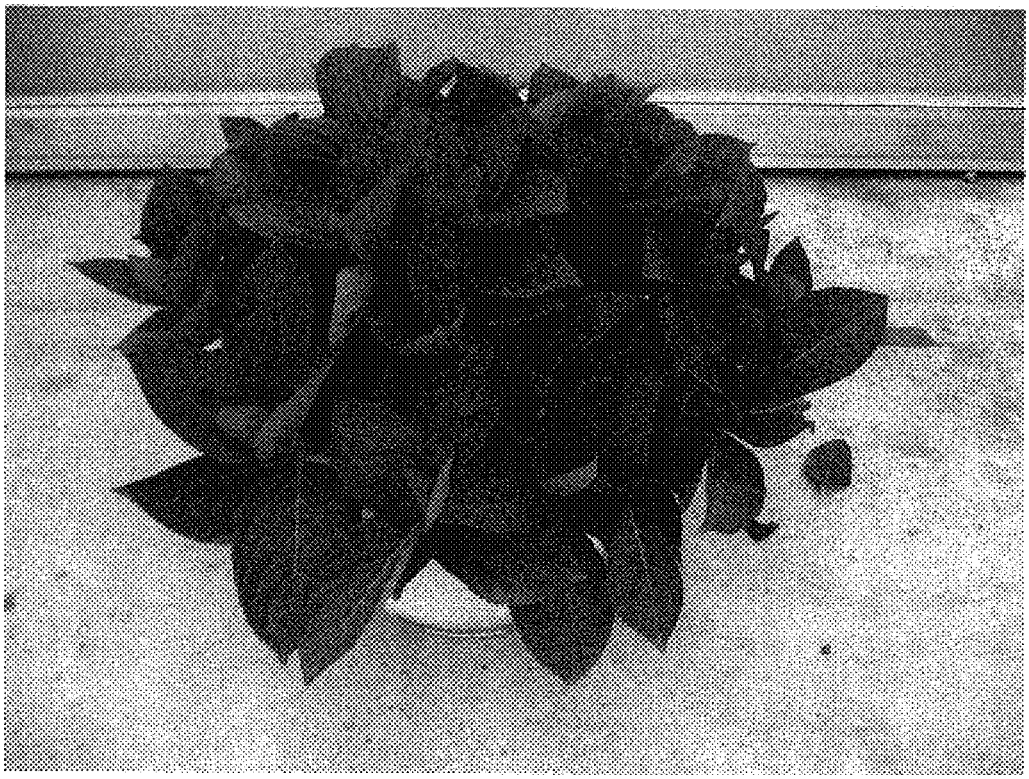
Figure 2:
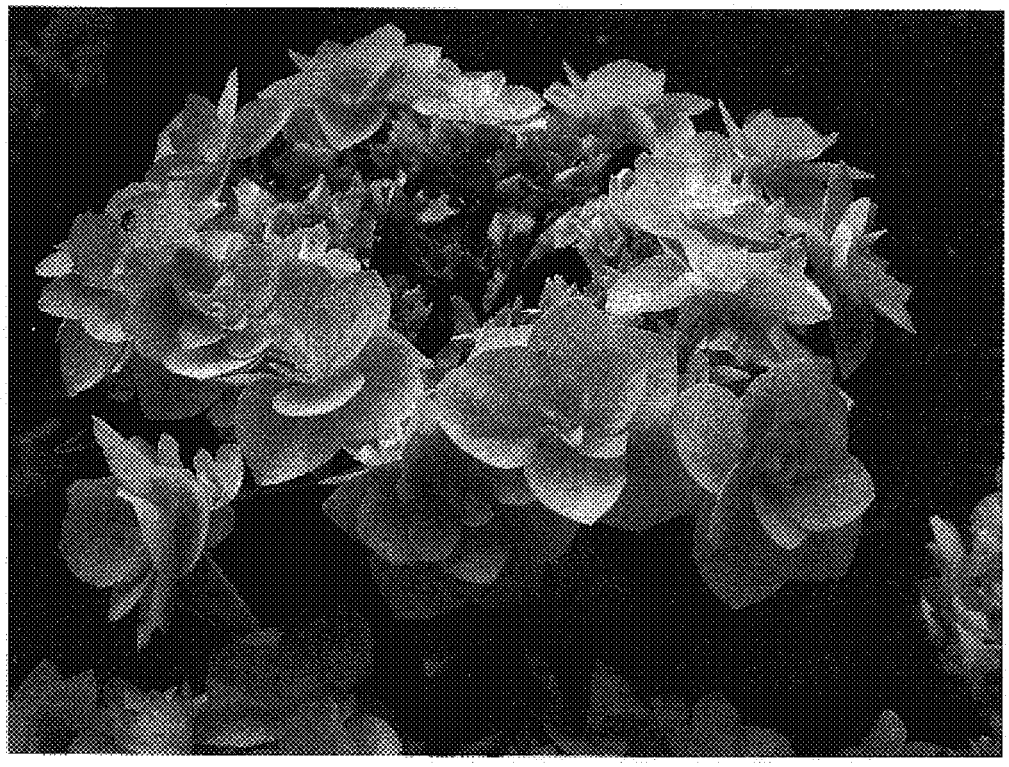

The drawing labeled as FIG. 2 illustrates a one year old plant of 'RIE 12' which has been grown in a 1.5 liter container in a frost-protected greenhouse in De Kwakel, The Netherlands. The plant was produced from a cutting which was rooted and grown in a four inch container, then transplanted into the 1.5 liter container and pinched to encourage basal branching. This drawing depicts the inflorescence of 'RIE 12' at three developmental stages, from first opening of an individual sterile flower to full development of the sterile flowers which are held above, and covering, the smaller fertile flowers.

All drawings were made using conventional techniques and although colors may appear different from actual colors due to light reflectance they are as accurate as possible, by conventional photography.

BOTANICAL DESCRIPTION OF THE PLANT

The following is the detailed description of 'RIE 12' as grown in a greenhouse in De Kwakel, The Netherlands. Data was collected in April 2004 from 2-year-old plants grown in 5-liter containers. The plants were growing in a peat-based medium and maintained within pH range 6.0-6.4. The color determinations are in accordance with the 2001 Edition of the Colour Chart of The Royal Horticultural Society, London, England, except where general color terms of ordinary dictionary significance are used. The growing requirements are similar to the species.

Botanical classification: *Hydrangea macrophylla* 'RIE 12'.
*Genus.*—*Hydrangea.*
*Species.*—*macrophylla.*
*Denomination.*—'RIE 12'.

Commercial classification: Floral plant, ornamental shrub.

Common name: *Hydrangea.*

Use: Grown for use as a potted indoor plant or as an outdoor ornamental flowering shrub.

Container size: Suggested container size is 1.5 liter or larger.

Cultural requirements: Performs best when planted in loam based moisture retentive soil, in partial shade, with regular water.

Parentage: *Hydrangea macrophylla* 'RIE 12' is a hybrid plant that resulted from the induced cross-pollination of the following parent plants:
*Female parent.*—An unnamed individual *Hydrangea macrophylla.*
*Male parent.*—An individual *Hydrangea macrophylla* 'Sumidanohanabi' (unpatented).

Plant description:
*Blooming seasons.*—Spring and summer (natural season) or year-round if forced.
*Plant habit.*—Broad upright.
*Plant type.*—Deciduous shrub.
*Overall plant shape.*—Broad inverted triangle.
*Vigor.*—Moderate.
*Growth rate.*—An average of 15-cm. per month in spring.
*Plant height.*—45 cm. in height.
*Plant diameter.*—61.5 cm. in diameter.
*Hardiness.*—USDA Zone 7.
*High temperature tolerance.*—Tolerant to 32° Centigrade.
*Root system.*—Fibrous.
*Propagation.*—Propagation is accomplished by the method of softwood cuttings.
*Time and temperatures to develop roots.*—Approximately 4 weeks is needed to develop roots on an initial cutting, at temperatures of 18° to 20° Centigrade.
*Crop time* (*outdoor plant crop*).—An average of 12 months is needed to produce a commercial container size flowering outdoor plant, from a rooted cutting.
*Temperatures* (*outdoor plant crop*).—From rooted cuttings to commercial size containers, the outdoor crop is grown at natural outdoor temperatures utilizing unheated greenhouses for winter protection.
*Crop time* (*indoor plant crop*).—An average of 4-6 months is needed to produce a commercial container size flowering indoor plant, from a rooted cutting.
*Temperatures* (*indoor plant crop*).—Transplant rooted cuttings to liner pots and keep for a minimum of 6 weeks at below 5° Centigrade to force dormancy. Transplant to 1.5-liter containers and keep at 18° to 25° Centigrade for a minimum or 10 weeks to produce commercial container size flowering plants.

*Disease and pest resistance or susceptibility.*—No susceptibility to pests or disease known to the inventor.

Stem:

*Lateral branches.*—Number: An average of 8 lateral branches. Dimensions: Average length 22.8 cm; average diameter 6 mm. Shape: Rounded. Surface: Slightly glossy. Pubescence: None observed. Strength: Strong. Color: 144B.

*Lenticels.*—Present. Quantity: An average of 9 per cm of stem surface. Dimensions: Average length 2 mm; average width 0.5 mm. Color: N186C.

*Branching habit.*—Moderate to sparse basal branching.

*Branching requirements.*—Pinching encourages lateral branching.

*Internode length.*—5.1 cm between nodes.

Foliage:

*Type.*—Deciduous.

*Arrangement.*—Opposite.

*Division.*—Simple.

*Quantity of leaves per lateral stem.*—An average of 10 individual leaves per lateral stem.

*Leaf.*—Shape: Leaves range from broad oval to elliptic-oblong on an individual plant. Dimensions: Average length 12.2 cm; average width 8.5 cm. Apex: Apiculate. Base: Attenuate. Margins: Serrate. Appearance (adaxial and abaxial surfaces): Smooth, semi-glossy surfaces. Pubescence: None present. Venation pattern: Pinnate. Vein color (abaxial and adaxial surfaces): 145B. Leaf color (adaxial surfaces): 139A, but slightly darker. Leaf color (abaxial surfaces): 137C.

*Attachment.*—Petiolate.

*Petiole.*—Dimensions: Average length 1.7 cm; average diameter 3 mm. Surface: Glabrous. Shape: Cylindrical. Color: 144B.

*Durability of foliage to stress.*—High durability to stress.

*Stipules, tendrils, thorns.*—None observed.

*Fragrance.*—None observed.

Flowers:

*Flower arrangement.*—Terminal inflorescence.

*Inflorescence type.*—Compound corymb. one inflorescence per stem.

*Inflorescence dimensions.*—Average height 13.3 cm; average diameter 20.1 cm.

*Quantity of flowers per inflorescence.*—an average of 175 deformed fertile flowers and 190 sterile flowers.

*Flowering habit.*—An individual plant blooms continuously from early April to October.

*Bud.*—Dimensions: 3 mm in length; 2.5 mm in diameter. Shape: Ovate. Apex: Obtuse. Color: 145A.

*Flower aspect (fertile flowers).*—Flowers range from upward facing on an individual plant.

*Flower aspect (sterile flowers).*—Sterile flowers are slightly drooping.

*Rate of opening (fertile and sterile flowers).*—An average of 10% of the flowers on an individual plant open at once, and all the flowers on an individual plant have opened by 6 weeks.

*Flower shape (fertile and sterile flowers).*—Rotate in shape.

*Persistent or self-cleaning (fertile and sterile flowers).*—Persistent.

*Peduncle.*—Shape: Cylindrical. Dimensions: Average length 10.8 cm; average diameter 3.5 mm. Color: 144A. Surface: Puberulent. Angle: Average angle is 27.5°. Strength: Strong.

*Lenticels.*—Present on peduncle. Color: N186B. Dimensions: 0.75 mm. in height, 2 mm in width.

*Pedicels (on fertile and sterile flowers).*—Present.

*Lastingness of flowers.*—An individual flowers lasts 4 weeks.

*Flower response time.*—An average of 9 weeks.

*Flower fragrance.*—None observed.

*Fertile flowers.*—Dimensions: Average diameter 6 mm; average height 5 mm. Petal: Appearance: Dull. Surface: Glabrous. Number: An average of 4 petals per flower. Fused or unfused: Unfused. Shape: Ovate to irregular ovate. Margin: Entire. Apex: Acute. Dimensions: Average length 4 mm; average width 2.5 mm. Color (abaxial and adaxial surfaces when opening): 73D with 145C and 145D. Color (abaxial surfaces when fully opened): 75D. Color (adaxial surfaces when fully opened): 75D with 145D. Calyx: Present. Shape: Campanulate. Dimensions: Average length 2.5 mm; average diameter 4 mm. Sepals: Number: 8. Dimensions: Average length 2 mm; average diameter 1 mm. Color (abaxial and adaxial surfaces): 145A and 145B with 145D at the base. Fused or unfused: Fused. Shape: Ovate. Margin: Entire. Apex: Acute. Base: Cuneate. Appearance: Slightly glossy. Surfaces (adaxial and abaxial surfaces): Smooth. Pedicel: Dimensions: Average length 3.5 mm; average diameter 1 mm. Angle: Average angle is 27.5°. Strength: Moderate to strong. Color: A combination of colors 144A and 144B is present on an individual pedicel. Pedicel surface: Puberulent. Lenticels: None observed on pedicels of fertile flowers.

*Sterile flowers.*—Dimensions: Average diameter 5.4 cm; average depth 2.1 cm. Tepal: Dimensions: Average length 2.6 cm; average width 2.2 cm. Appearance: Dull. Surface: Glabrous. Number: An average of 16 tepals per sterile flower. Fused or unfused: Unfused. Shape: Range from rhomboidal to broad elliptic on an individual inflorescence. Margin: Entire. Apex: Rounded to bluntly acute. Color (abaxial and adaxial surfaces when opening): 73D. Color (abaxial surfaces when fully opened): 75B. Color (adaxial surfaces when fully opened): 75C. Calyx: None observed. Pedicel: Dimensions: Average length 3.5 cm; average diameter 2 mm. Angle: Average angle is 45°. Strength: Moderate to strong. Color: 75D. Surface: Glabrous. Pubescence: None observed. Lenticels: None observed.

Reproductive organs:

*Stamens.*—None observed.

*Anthers.*—None observed.

*Pistil.*—Present.

*Pistil number.*—An average of 4 present per individual fertile flower.

*Pistil length.*—An average of 2 mm. in length.

*Stigma.*—Present.

*Stigma shape.*—Club shaped.

*Stigma color.*—N78D.

*Style length.*—An average of 1.5 mm. in length.

*Style color.*—A combination of colors 145C and 145D.

*Ovary.*—Present on fertile flowers.

*Ovary position.*—Inferior.

*Ovary color.*—145C and 145D.

*Ovary dimensions.*—0.2 mm. in height and 0.2 mm. in diameter.

*Ovary shape.*—Globular.

Seed production: No seed production has been observed to date.

It is claimed:

1. A new and distinct cultivar of *Hydrangea* plant named 'RIE 12' as described and illustrated herein.

* * * * *